United States Patent [19]

Suhajda

[11] Patent Number: 4,675,504
[45] Date of Patent: Jun. 23, 1987

[54] ELECTRIC FOGGER

[75] Inventor: John I. Suhajda, Racine County, Wis.

[73] Assignee: S. C. Johnson & Son, Inc., Racine, Wis.

[21] Appl. No.: 876,584

[22] Filed: Jun. 20, 1986

[51] Int. Cl.$^4$ .................. A01M 1/20; A61L 9/03; F22B 1/28

[52] U.S. Cl. .................. 219/272; 219/275; 43/129; 239/136; 422/306

[58] Field of Search .............. 219/271, 272, 273, 274, 219/275, 276; 422/305, 306, 125; 239/135, 137, 44, 47, 51.5, 53, 54, 55, 56, 57, 58, 59, 60; 43/129

[56] References Cited

U.S. PATENT DOCUMENTS

| | | | |
|---|---|---|---|
| 1,990,338 | 2/1935 | Lippert | 219/271 |
| 2,269,689 | 1/1942 | Reichold | 219/435 |
| 2,543,052 | 2/1951 | Park | 219/433 |
| 2,660,828 | 12/1953 | Abrams | 219/272 |
| 2,667,567 | 1/1954 | Buehler | 219/272 |
| 2,675,293 | 4/1954 | Baker | 422/4 |
| 2,685,020 | 3/1954 | Laibow | 219/275 |
| 2,690,500 | 9/1954 | Winberg et al. | 219/272 |
| 2,767,511 | 10/1956 | Kissner et al. | 43/125 |
| 2,784,466 | 3/1957 | Burns, III | 219/272 |
| 3,002,080 | 9/1961 | Heinzig | 219/275 |
| 3,080,624 | 3/1963 | Weber, III | 422/125 |
| 3,548,533 | 12/1970 | Jensen | 43/129 |
| 3,727,840 | 4/1973 | Nigro | 239/57 |
| 3,872,280 | 3/1975 | Van Dalen | 219/271 |
| 3,903,883 | 9/1975 | Pecina et al. | 128/193 |
| 3,986,670 | 10/1976 | Syveson | 239/133 |
| 4,163,038 | 7/1979 | Nishimura et al. | 422/36 |
| 4,203,027 | 5/1980 | O'Hare et al. | 219/275 |
| 4,326,119 | 4/1982 | Swiatosz | 219/272 |
| 4,391,781 | 7/1983 | van Lit | 422/125 |
| 4,399,351 | 8/1983 | Koff | 219/433 |
| 4,544,592 | 10/1985 | Spector | 239/56 |
| 4,571,485 | 2/1986 | Spector | 219/272 |

FOREIGN PATENT DOCUMENTS 547130 9/1931 Fed. Rep. of Germany ........ 239/44

Primary Examiner—E. A. Goldberg
Assistant Examiner—Teresa J. Walberg

[57] ABSTRACT

An electric fogger includes a housing having a heat source, a timer and a disposable canister containing a fog-producing material such as an insecticide, deodorant, perfume, disinfectant or air freshener. The housing includes a top member and a base member capable of receiving and replaceably holding the disposable canister. The housing contains the heat source such as a hot plate, for heating the insecticide or the like in the canister; a printed circuit board including an electrical switch for activating the heat source and a timer which automatically turns the heat source off after a predetermined period of time; and a pivoting cam adapted to engage the electricl switch on the printed circuit board to allow electricity to flow to the heat source when the pivoting cam engages a lug on the canister upon insertion of the canister into the housing. The fogger is of simple construction and is easy and safe in operation.

13 Claims, 9 Drawing Figures

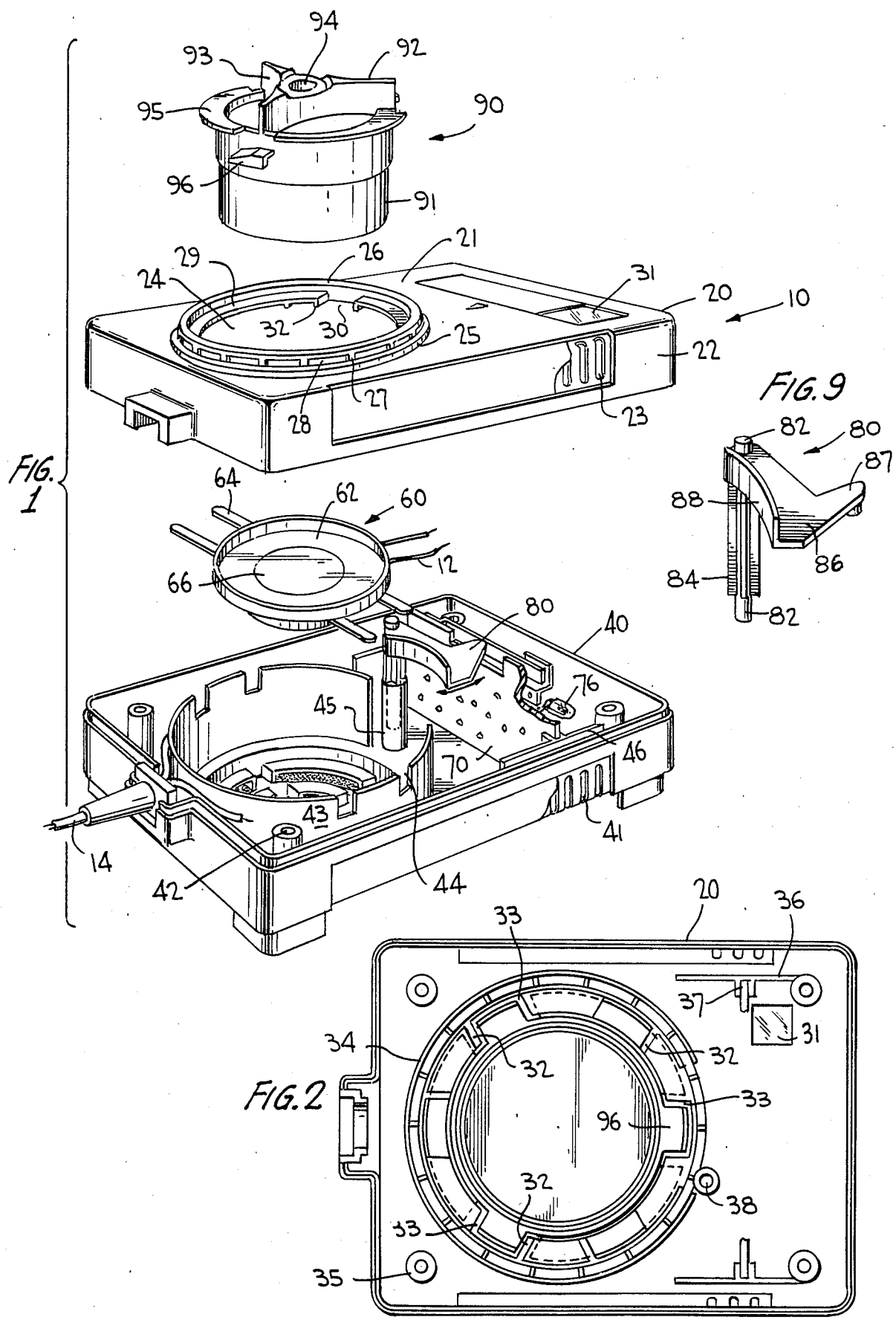

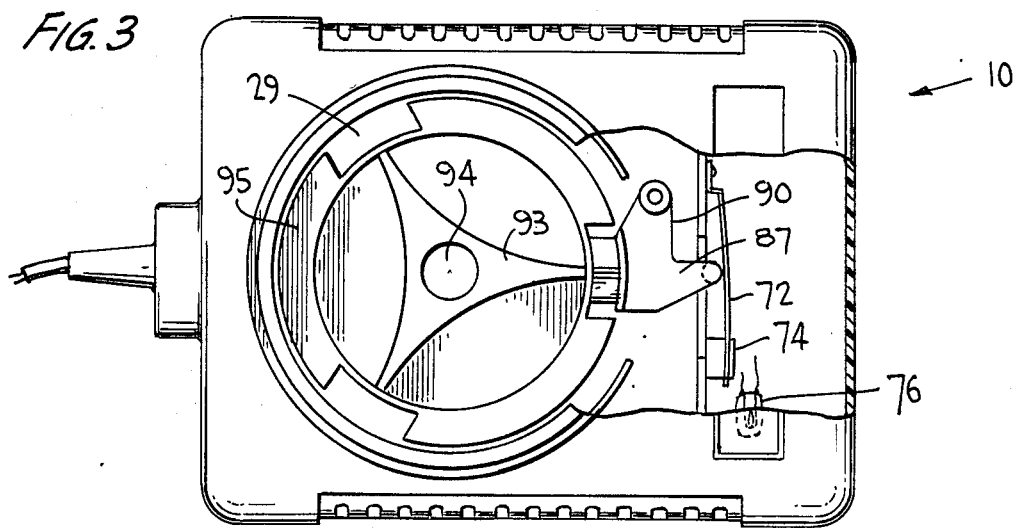
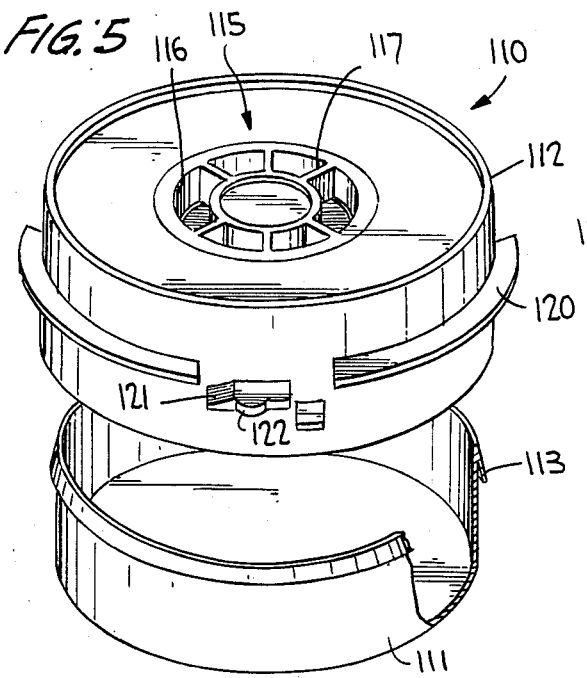
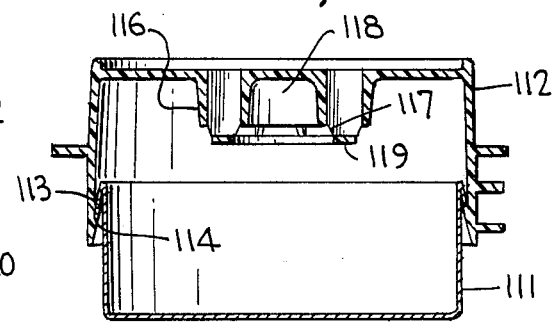
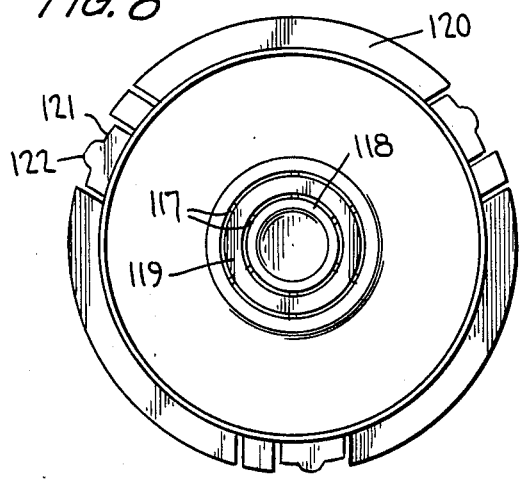
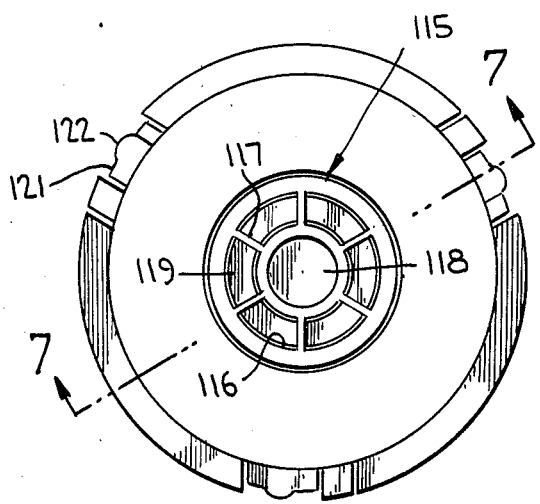

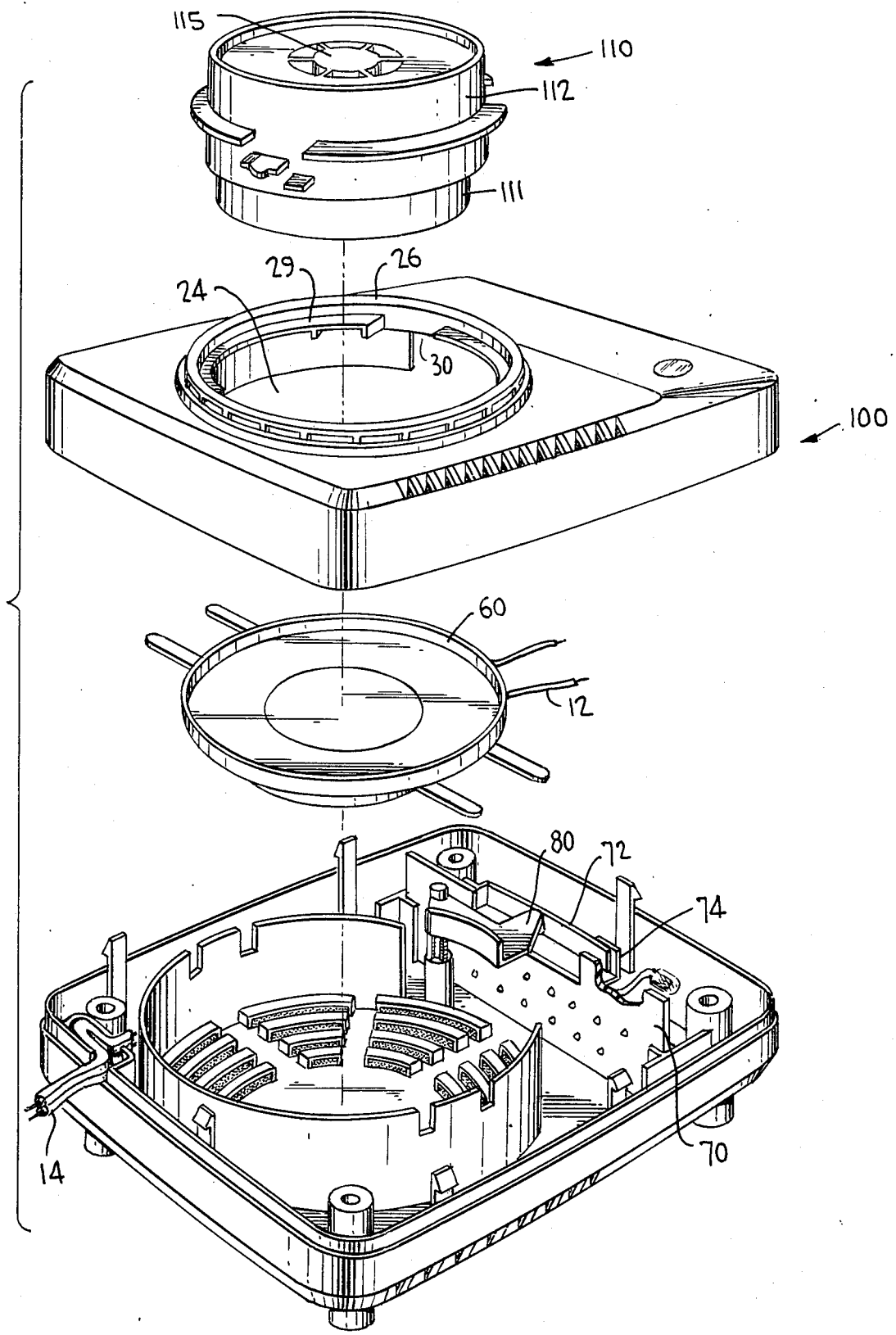

ELECTRIC FOGGER

FIELD OF INVENTION

This invention relates generally to an electric fogger apparatus for fogging materials such as insecticides, deodorants, perfumes, disinfectants, and air fresheners. In particular, this invention relates to an electric fogger for the fogging of an insecticide which includes a housing with a heat source and a timing means and a disposable canister containing an insecticide for fogging whereby upon insertion of the canister into the housing, the canister simultaneously activates the electric fogger and locks the canister into position in the electric fogger.

BACKGROUND OF INVENTION

A wide variety of electric devices are known in the art for dispensing of insecticides. However, the known electric devices are, for the most part, complex devices which are expensive to manufacture and do not provide for ease of operation by the user. Specifically, the majority of electric devices require that the user return to the device and turn the device off after the insecticide is released or require that the user physically handle the insecticide material.

Electric devices are known which plug directly into the wall, such as U.S. Pat. No. 4,391,781, assigned to S. C. Johnson & Son, Inc., containing an insecticide impregnated mat which is inserted into the housing of the device adjacent to an electric heater for generating a sustained level of insecticide to the atmosphere. This type of device, while extremely useful for certain applications, requires that the consumer insert an insecticide impregnated mat into the device, plug the device into an electric outlet, and return and remove the device from the electric outlet after the insecticide is dispensed. While having been found useful and successful for certain applications, such devices preclude the use of larger amounts of an insecticide, do not allow the user to avoid handling the insecticide, and do not turn off automatically after the insecticide has been dispensed.

Electric insecticide generators are also known in the art having more complex constructions and which are plugged into an electric outlet by means of an electric cord and plug such as disclosed in U.S. Pat. Nos. 2,675,293; 2,685,020; 2,767,511; and 2,690,500. These patents disclose complex structures which are expensive to manufacture, inconvenient to use in many circumstances, and potentially unsafe. For example, the insecticide of these devices is exposed directly to the user, allowing for possible spilling of the insecticide or burning of the user. Further, after generation of the insecticide is complete, the user must manually turn the devices off.

Electric insecticide generators are known in the art, such as U.S. Pat. No. 2,660,828, which use a timer wherein the timer is present to open the electric circuit to turn off the device. Cooking appliances are also known in the art such as U.S. Pat. Nos. 2,543,052 and 2,269,689, in which a pot or pan activates the appliance or is locked to the appliance. However, these prior art devices are generally complex and expensive to manufacture, and impractical to use.

Further, fog-producing materials are known in the art. For example, U.S. Pat. No. 4,163,038 discloses the use of a mixture of a fog-producing material, such as an insecticide, a fungicide, an antiseptic, a plant growth regulant, a herbicide, or a repellant, and a blowing agent in an electric device for dispensing the fog-producing material.

There are no known prior art electric foggers which are activated by the insertion of a disposable canister containing an insecticide whereby the canister simultaneously activates the electric fogger and locks the canister into position, and then automatically turns the fogger off after completion of the fogging of the insecticide.

Accordingly, the prior art insecticide generators have generally been complex both in their manufacture and use. The prior art insecticide generators have not provided the user with a simply constructed fogger which the user can activate by the insertion of an insecticide containing canister and which will turn off automatically after the insecticide has been completely dispensed.

PRIMARY OBJECTS AND SUMMARY OF THE INVENTION

The present invention overcomes the disadvantages of the devices of the prior art, including those mentioned above, in that it comprises a novel relatively simple electric fogger for the fogging of an insecticide or other evaporable material.

Accordingly, it is an object of the invention to provide for an electric fogger comprising a housing with a heat source and timing means and a disposable canister containing a fog-producing material which is simple in construction and easy to use.

It is a further object of the invention to provide an electric fogger which has means for receiving and replaceably holding a disposable canister whereby upon insertion of the canister in the housing the canister has means for activating the fogger and simultaneously locks the canister into the housing.

It is a further object of the invention to provide an electric fogger having a housing and a disposable canister whereby the canister activates the fogger and the fogger contains a timing means for automatically turning the fogger off after the insecticide has been fogged.

It is a further object of the invention to provide an electric fogger which is capable of receiving and replaceably holding a disposable canister containing an insecticide which contains a pivoting cam which activates an electrical switch to turn the fogger "on" upon insertion of the disposable canister.

It is a further object of the invention to provide a disposable canister for use in an electric fogger which retains the insecticide from contact by the user and which allows the insecticide to evaporate to the environment of use through an opening in the canister.

It is a further object of the invention to provide a disposable canister for use in an electric fogger which contains an opening having a baffle configuration which prevents the spitting of any unevaporated insecticide into the environment of use while allowing the release of the fogged material.

It is a further object of the invention to provide an electric fogger which is safe to use due to the nonexposure of the insecticide or the electric components of the device to the user.

The electric fogger of the invention comprises a housing having a heat source and a timing means and a disposable canister containing a fog-producing or evaporable material such as an insecticide, deodorant, perfume, disinfectant or air freshener. The housing is comprised of a top member and a base member capable of receiving and replaceably holding the disposable canister. The housing contains a heating means such as a hot plate, for heating the insecticide in the canister; a printed circuit board containing an electrical switch for activating the heating means and a timer which automatically turns the heating means off after a predetermined period of time; and a pivoting cam adapted to engage the electrical switch on the printed circuit board to allow electricity to flow to the heating means wherein the pivoting cam engages the electrical switch in response to contact from a lug on the canister upon insertion of the canister into the housing.

The disposable canister of the electric fogger which contains an evaporable material comprises a container to hold a fog-producing material and which is constructed of a material capable of transferring heat from a heat source to the fog-producing material, and a cap having at least one opening to allow the release of a fog and one or more lugs which serve to activate the electric fogger when placed in the fogger. The canister of the invention provides for the simultaneous activation of the electric fogger and the locking of the canister into the housing of the electric fogger.

The invention also includes a non-spitting disposable canister containing a fog-producing material which will allow the release of the fog but which prevents the release or spitting of any unevaporated fog-producing material. The non-spitting disposable canister which comprises a container which holds a fog-producing material is constructed of a material which is capable of transferring heat from a heat source to the fog-producing material, including a cap having an opening with baffle means constructed and arranged therewith to allow the release of the fog but which prevents the release of any unevaporated fog-producing material. Additionally, the baffle prevents any active material from falling out of the canister if the canister is inverted before or during activation. Also, the baffle prevents the addition of extraneous materials into the canister. The canister again includes one or more lugs which serve to activate the electric fogger and simultaneously lock the canister into the housing of the electric fogger. The baffle means comprises a cylindrical wall extending downwardly from the top of the cap and spoke members extending outwardly from the cylindrical wall to converge at and connect to an inner inverted cup. The spoke members extend below each of the cylindrical wall and inverted cup and are connected to a horizontally disposed ring member. The configuration of the baffle means provides indirect openings to the environment of use and thus prevents the spitting or release of any unevaporated fog-producing material, such as an insecticide, to the environment of use while allowing for the release of fogged material.

As used in the present invention, the term "fog-producing material" means a composition which evaporates upon heating or which undergoes a chemical reaction or decomposition of at least one component to produce a fog or aerosol to carry an active agent to the atmosphere. Examples of fog-producing materials include insecticides, repellants, perfumes, deodorants, disinfectants, etc. Preferred fog-producing materials are disclosed in U.S. Pat. No. 4,163,038.

The cap of the disposable canister also includes outwardly extending rims for seating the canister on the housing of the electric fogger in conjunction with the lugs of the cap for locking the canister into the housing.

BRIEF DESCRIPTION OF THE DRAWINGS

Other objects, advantages and novel features of the present invention will become apparent from the following detailed description of the invention when considered in conjunction with the accompanying drawing, in which like reference numerals designate like parts throughout the figures thereof, and wherein:

FIG. 1 is an exploded view of one embodiment of the invention;

FIG. 2 is a bottom view of the top member of the housing in receipt of the canister;

FIG. 3 is a top partially cut away view of the electric fogger shown being activated by the canister;

FIG. 4 is an exploded view of a second embodiment of the invention;

FIG. 5 is an exploded view of a preferred embodiment of the canister;

FIG. 6 is a top view of a preferred embodiment of the cap of the canister;

FIG. 7 is a cross-section of a preferred embodiment of the cap of the canister taken along line 7—7 of FIG. 6.

FIG. 8 is a bottom view of the cap of a preferred embodiment of the canister.

FIG. 9 is a plan view of the pivoting cam.

DETAILED DESCRIPTION OF THE INVENTION

Referring to FIG. 1, the electric fogger of the present invention comprises a housing 10 and disposable canister 90. Generally, housing 10 comprises a top 20 and a base 40. Housing 10 contains secured therein, as described more fully hereafter, pivoting cam 80, printed circuit board 70 (hereafter "PC board"), hot plate 60, electrical wires 12 connecting PC board 70 to hot plate 60 (not shown), and electrical cord 14 and plug (not shown) for insertion into an electrical outlet and connected to PC board 70 (not shown) for providing electricity to the fogger.

Top 20 and base 40 of housing 10 are made of any suitable material such as plastic or metal, a preferred material being plastic. Top 20 and base 40 are made by any conventional molding process and are constructed and arranged to mate together by any suitable fastening means. In the preferred embodiment, the fastening means are screws.

Top 20 of housing 10 is shown in top view in FIG. 1 and in bottom view in FIG. 2. Referring to FIG. 1, top 20 includes an outer surface 21 and side walls 22. Side walls 22 include grid openings 23 for ventilation of the heat generated from hot plate 60.

Top 20 further includes an opening 24 for receiving and replaceably holding canister 90. Opening 24 is shown and described in its preferred embodiment as being circular, although the configuration of the opening may be modified. Opening 24 has a neck 25 protruding outwardly and upwardly from surface 21. Attached to neck 25 is an annular ring 26 through legs 27. Neck 25, legs 27 and ring 26 provide for openings 28 for additional ventilation of heat generated by hot plate 60. Extending inwardly from ring 26 are flanges 29 for receiving and supporting canister 90. Flanges 29 are spaced sufficiently apart from one another to provide openings 30 for receiving lugs 96 of canister 90.

Housing 10 contains a window 31 for transmission of a light source 76 from printed circuit board 70 to indicate when the electric fogger is in operation.

Referring to FIG. 2, top 20 is seen in bottom view with canister 90 shown inserted and rotated in the housing to activate the electric fogger and lock canister 90 into position. A plurality of stops 32 extend downwardly from flanges 29. Stops 32 are constructed to permit canister 90 to be rotated in only one direction and to seat lugs 96 after being rotated approximately 1/6th of a turn. Rotation of the canister only a predetermined distance is essential to activate the electric fogger by having one of lugs 96 contact pivoting cam 80 which in turn contacts leaf spring 72 on PC board 70 to close the electrical circuit. Further, the stop members aid in locking the canister into the housing.

Flanges 29 further include a plurality of detents 33 for receiving and seating lugs 96. Lugs 96 will be positioned in detents 33 when the canister is rotated approximately 1/6th of a turn thereby activating the canister and locking the canister into the housing.

Top 20 further includes a heat shield 34 which surrounds hot plate 60 and mates with heat shield 43 of base 40. The shield serves to retain the heat from hot plate 60 within a confined area and to direct the heat to the canister 90.

Bosses 35 are provided for fastening top 20 to base 40 by screws (not shown), or any other suitable fastening means, and are located in top 20 in mating relation to corresponding bosses 42 in base 40. Vertical walls 36 and guide channels 37 are provided for receiving and holding PC board 70 in place in the housing. Slot 38 is provided for receiving and holding the top of pivoting cam 80 in the housing.

Base 40 of housing 10 is shown in FIG. 1. As described above, the base 40 mates with the top 20. Similar to top 20 base 40 is generally rectangular and contains a bottom surface and side walls. Ventilation grid openings 41 are located in the sides of base 40 for ventilation of heat generated from hot plate 60. A ventilation grid opening is preferably also located in the bottom of the base 40 (not shown).

Base 40 includes bosses 42 which mate with bosses 35 of top 20 through which screws (not shown) are inserted for fastening base 40 to top 20. The base has a heat shield 43 which serves to receive, support, and surround hot plate 60. Notches 44 are provided in shield 43 for receiving arms 64 of hot plate 60. A hollow column 45 is located adjacent to shield 43 and PC board 70 for receiving and supporting pivoting cam 80. Vertical walls 46 with guide channels (not shown) are provided in base 40 for receiving and holding PC board 70 in position in the housing.

Electric heating elements are generally known in the art and any conventional heating element may be used in conjunction with the invention. A preferred heating element is a hot plate. Hot plate 60 comprises a lightweight metal plate 62 with arms 64 and heater 66. Heater 66 is attached to metal plate 62 by any suitable fastening means and may be any conventional electric heater known in the art, for example a TDK ® Model No. 5001 heater has been found to work well, also a rope heater can be used. Electrical wires 12, attached to electrical contacts (not shown) on PC board 70, are attached to electrical contacts (not shown) on the underside of heater 66 and deliver electric current to the heater to energize the heater. PC board 70 controls the electric current delivered to the heater.

Referring again to FIG. 1, PC board 70 is a conventional printed circuit board known in the art and is adapted to operate and control the electric current delivered to heater 66. The PC board serves to turn the heater "on" by means of an electrical switch attached to the PC board and turn the heater "off" by means of a timer incorporated in the PC board. Specifically, a timer is incorporated in the PC board to control the period of time which the heater 66 is in operation. Any conventional timer known in the art may be incorporated in the PC board. The timed period is adjusted to correspond to the amount of time needed to evaporate the insecticide in canister 90. A conventional electric cord 14 and plug (not shown) is attached to electric contacts on the PC board to provide electric current to the fogger. The electric cord 14 is plugged into a conventional electric outlet.

As best shown in FIG. 3, the PC board may use a conventional electrical switch known in the art for closing an electrical circuit and to deliver electricity to the fogger. A preferred electrical switch for closing the electrical circuit and turning the device "on" is leaf spring 72 and contact 74. When leaf spring 72 is placed in electrical contact with contact 74, the electrical circuit is closed and the PC board energizes heater 66. A timer on the PC board (not shown) is set for a predetermined period of time which upon expiration will break the electrical circuit thereby turning "off" the heater 66.

PC board 70 also may include a light source 76 which is positioned adjacent to window 31 for indicating when the device is in operation.

Referring to FIGS. 1 and 9, pivoting cam 80 is located adjacent to PC board 70 and serves to close the electrical circuit upon insertion and rotation of canister 90 by moving leaf spring 72 into electrical contact with contact 74 thereby turning "on" the electric fogger. Pivoting cam 80 is secured in the housing by column 45 of base 40 and slot 38 of top 20. Pivoting cam 80 includes a cam post 82 which is generally cylindrical for insertion in cam support column 45 and retaining slot 38. Cam post 82 may include support arms 84 extending outwardly and away from cam post 82 for supporting the pivoting cam on column 45 and for supporting cam arm 86. Cam arm 86 is generally L-shaped and has a finger 87 for contacting leaf spring 72 to close the electrical circuit and has a concave vertical wall camming surface 88 opposite of finger 87 for engagement with lug 96. In activating the fogger as shown in FIG. 3, a lug 96 of canister 90 will contact camming surface 88 to pivot the cam post 82 in column 45 thereby pivoting cam arm 86 into contact with leaf spring 72 to close the electrical circuit and energize the fogger. The lug 96 will remain in contact with camming surface 88 keeping the electrical circuit closed until the canister is removed by the user. As described above, the electrical circuit will be broken by a timer incorporated in the PC board after a predetermined period of time thereby automatically turning the fogger "off."

Canister 90, as best shown in FIGS. 1 and 3, is comprised of a container 91, preferably made of a lightweight metal, and a cap 92, preferably made of plastic. The canister may contain any suitable fog-producing or evaporable material known in the art such as an insecticide, a deodorant, a perfume, a disinfectant, or an air freshener for fogging or dispensing upon exposure to heat. The container 91 must be capable of receiving heat and transferring the heat to the material in container 91. The cap 92 is attached to the container by conventional means. Cap 92 has ribs 93 for rotating the canister after insertion in the housing to activate the electric fogger and to lock the canister into position in the housing. Cap 92 has a small opening 94 in the center of the cap for release of the material.

As also seen in FIGS. 1 and 3, cap 92 includes collar members 95 extending from the cap for seating on flanges 29 of top 20. Cap 92 also includes lugs 96 extending from the base of cap 92. The lugs 96 serve to simultaneously activate the electric fogger by contacting pivoting cam 80 to close the electrical circuit and to lock the canister into the housing.

As seen in FIGS. 2 and 3, the canister is inserted into the housing 10 by inserting lugs 96 through openings 30 and collars 95 seat on flanges 29. The canister is rotated approximately 1/6th of a turn whereby one of lugs 96 will activate the electric fogger by contacting pivoting cam 80 which closes the electrical circuit. Lugs 96 in conjunction with collars 95 and flanges 29 serve to lock the canister into the housing.

FIG. 4 illustrates a second preferred embodiment of the invention described above. The embodiment shown in FIG. 4 uses generally the same components as the electric fogger shown in FIG. 1 and operates on the same principles as the electric fogger shown in FIG. 1. However, the housing 100 and canister 110, as shown in FIGS. 5, 6, 7, and 8, are of a modified construction than the housing 10 and canister 90 of FIG. 1. Since the housing 100 and its component parts shown in FIG. 4 are essentially the same as those previously described for the electric fogger shown in FIG. 1, the description will not be repeated, it being understood that the electric fogger shown in FIG. 4 is constructed and operates on the same principles as the electric fogger shown in FIG. 1.

Referring to FIGS. 5, 6, 7, and 8, canister 110 includes a container 111, preferably made of a lightweight metal, and a cap 112, preferably made of plastic or any other suitable material. The canister may contain any suitable fog-producing or evaporable material known in the art such as an insecticide, a deodorant, a perfume, a disinfectant, or an air freshener for dispensing upon exposure to heat. The container must be capable of receiving heat and transferring the heat to the material contained therein. The cap is preferably made of plastic by conventional molding processes. Container 111 is attached to cap 112 by means of a lip 113 surrounding the periphery of the container which catches on a ledge 114 on the inside of cap 112. Cap 112 includes a baffle opening 115 which prevents the spitting of any unevaporated fog-producing material from the canister while allowing for the release of the fogged material. Baffle opening 115 includes a cylindrical wall 116, as best shown in FIGS. 5 and 7, extending downwardly from the top of the cap having an open top and bottom. Extending outwardly from cylindrical wall 116 are spokes 117 which converge at and connect to an inner inverted cup 118. Spokes 117 extend below each of cylindrical wall 116 and inverted cup 118. Connected at the bottom of spokes 117 is a horizontally disposed ring 119 which is arranged to provide a space between it and the inverted cup 118. Baffle opening 115 provides a configuration which prevents the spitting of any insecticide, or other fog-producing material, while allowing release of the fogged material. Also, wall 116 prevents the release of any liquid if the canister is tipped or inverted.

Cap 112 also includes collars 120 extending outwardly from the cap for seating on flanges 29 of the housing as described above. Further, cap 112 includes lugs 121 extending outwardly from the cap for activating the electric fogger and locking the canister into the housing of the electric fogger as described above. Lugs 121 further include nipples 122 protruding from the lugs for contacting pivoting cam 18 and for seating in detents 33.

Referring again to FIGS. 5 through 8, canister 110 may be used in electric foggers having a separate power and timer means. For use in such an embodiment, cap 112 has a second set of lugs 123 extending outwardly from cap 112 and constructed and arranged below lugs 121. Lugs 123 are provided to activate a second electrical switch. For example, when a PC board is not used, the electric fogger may use a separate timer means and power source. In such a case, housing 100 may include a power source activated by a first electrical switch and a timer means activated by a second electrical switch. Thus for example, upon insertion and rotation of canister 110, lugs 121 will activate the first electrical switch to turn the fogger "on" and lugs 123 will activate the second electrical switch to set the timer means, the timer means being constructed to open the electrical circuit after a predetermined period of time.

Having described the preferred embodiments of the invention, the operation of the electric fogger will now be described in reference to the embodiment shown in FIGS. 1–3. To use the electric fogger described herein, the user plugs electric cord 14 into an electric outlet. Canister 90 is then inserted into housing 10 after lining up lugs 96 with openings 30. Collars 95 of canister 90 seat on and overlie flanges 29 of housing 10. Canister 90 is rotated clockwise approximately 1/6th of a turn whereby lugs 96 are seated in detents 33 as shown in FIG. 2. One of lugs 96 will pivot cam 80 into contact with leaf spring 72 thereby closing the electrical circuit on PC board 70 allowing the electric current to pass to heater 66 thereby activating the electric fogger. Rotation of canister 90 simultaneously activates the electric fogger and locks the canister into the housing as lugs 96 are seated in detents 33 beneath flanges 29 and collars 95 are seated on top of flanges 29 thereby holding the canister in the housing. The hot plate will then heat up and provide heat to container 91 of the canister which is transferred to the fog-producing material in the container thereby causing evaporation of fog-producing material to produce a fog which is released through opening 94 to the environment of use. The timer of PC board 70 is set to correspond to the amount of time required to completely fog the fog-producing material and at the end of such period will automatically break the electrical circuit thereby turning the heater "off." "After the insecticide is completely fogged, the fogger automatically turns off allowing the user to return and remove the exhausted canister at his convenience. The exhausted canister is removed by rotation of the canister counter-clockwise and is disposed of. The fogger is then ready for the insertion of a new canister.

As described above and shown in FIGS. 5 through 8, the electric fogger may utilize canister 110 having baffle opening 115 which prevents the spitting of unevaporated insecticide into the environment of use while allowing the release of the fogged material. Canister 110 is a preferred embodiment for the disposable canisters.

The above-described invention provides an electric fogger which is inexpensive to manufacture and easy and safe to use. The electric fogger avoids user contact with the fog-producing material and allows the user to activate the fogger and leave the room knowing that the device will turn "off" automatically upon complete fogging of the fog-producing material. While the preferred embodiments of the device have been described in detail above, various modifications and variations of the invention are possible in light of the above teachings. It is, therefore, to be understood that within the scope of the appended claims the invention may be practiced otherwise than as above-described.

It is claimed:

1. An electric fogging apparatus comprising:
   (a) a housing;
   (b) a canister for removable insertion into said housing comprising
      (1) a container containing a fog-producing material and constructed of a material which will transfer heat to said fog-producing material, and
      (2) a cap attached to said container, said cap having an opening to allow for the release of a fog from within the container and having one or more lugs extending from said cap for locking said canister into said housing;
   (c) a means on said housing for receiving and replaceably holding said canister in said housing;
   (d) an electrical heating means in said housing for heating said canister in said housing;
   (e) electrical timing means within said housing which controls said heating means whereby said heating means is operated for a predetermined period of time; and
   (f) electrical switch means constructed and arranged with said timing means and said heating means for activating said timing means and said heating means, said switch means being activated by one of said lugs on said canister upon insertion and rotation of said canister in said receiving and holding means of said housing;
thereby heating said canister, the heat being transferred to said fog-producing material to produce a fog which is released to an environment of use through the opening in said canister cap.

2. An electric fogging apparatus according to claim 1 wherein said housing comprises a molded plastic top and a molded plastic base held together by a fastening means.

3. An electric fogging apparatus according to claim 1 wherein said means for receiving and replaceably holding said canister comprises an opening in the top of said housing including at least one flange extending from said opening, said flange being constructed to have at least one space in said flange adapted to receive one of said lugs from said canister, when said canister is inserted into said opening with the lug of said canister being in corresponding relation to the space provided by said flange.

4. An electric fogging apparatus according to claim 1 wherein said means for heating said canister comprises an electric hot plate.

5. An electric fogging apparatus according to claim 1 wherein said timing means comprises a timer incorporated in a printed circuit board.

6. An electric fogging apparatus according to claim 5 wherein said electrical switch means comprises a leaf spring and a contact attached to a printed circuit board and a pivoting cam which contacts said leaf spring which engages said contact thereby closing the electrical circuit and energizing the fogger.

7. An electric fogging apparatus according to claim 1 wherein the opening of the cap of said disposable canister includes baffle means which allows the release of the fog and prevents the spitting or release of any unevaporated fog-producing material.

8. An electric fogging apparatus according to claim 7 wherein said baffle means of the disposable canister comprises a cylindrical wall extending downwardly from the top of said cap, two or more spokes extending outwardly from said cylindrical wall and converging at and connected to an inverted cup, said spokes further being attached to a horizontally disposed ring at the base of said spokes, whereby said baffle means allows the release of the fogged material while preventing the spitting of any fog-producing material.

9. A fog-producing canister for use in an electric fogger comprising:
   (a) a container having an open top which holds a fog-producing material and which is constructed of a material which will transfer heat from a heat source to said fog-producing material; and
   (b) a cap attached to said container for covering said container having an opening to allow the release of a fog and having at least one lug extending from said cap for activating said electric fogger.

10. A fog-producing disposable canister according to claim 9 wherein the opening of the cap of said disposable canister includes baffle means which allows the release of the fog and prevents the release or spitting of any unevaporated fog-producing material.

11. A fog-producing disposable canister according to claim 10 wherein said baffle means comprises a cylindrical wall extending downwardly from the top of said cap; two or more spokes extending outwardly from said cylindrical wall and converging at and connected to an inverted cup, said spokes further being attached to a horizontally disposed ring at the base of said spokes, whereby said baffle means allows the release of the fogged material while preventing the spitting or release of any unevaporated fog-producing material.

12. A fog-producing disposable canister according to claim 9 wherein said cap has a first set of lugs extending outwardly from said cap to activate a power source in said electric fogger and a second set of lugs constructed and arranged either above or below said first set of lugs to activate a timer means in said electric fogger whereby said fogger is operated for a predetermined period of time.

13. An electric fogging apparatus comprising:
   (a) a molded plastic housing consisting of a base member and a top member;
   (b) a disposable canister for removable insertion into said housing comprising
      (1) a container which holds a fog-producing material and is constructed of a material which will transfer heat from a heat source to said fog-producing material, and
      (2) a cap attached to said container, said cap having an opening to allow for the release of a fog and having one or more lugs extending from said cap for locking said canister into said housing;
   (c) an opening in said top member of said housing for receiving and replaceably holding said disposable canister said opening being bounded by at least one flange, said flange having at least one space for receipt of a lug from said canister;

(d) an electric hot plate secured in the base of said housing under said opening in said housing for supporting and heating said disposable canister;

(e) a printed circuit board located in said housing including (1) an electrical switch comprising a leaf spring and a contact whereby said leaf spring contacts the contact to close the electrical circuit allowing the flow of electricity to said hot plate; and (2) a timing means whereby said hot plate is operated for a predetermined period of time; and (f) a pivoting cam in said housing constructed and arranged to engage simultaneously one of said lugs on said canister upon insertion and rotation of said canister in said opening of said housing and said electrical switch means to activate said hot plate; thereby heating said canister, the heat being transferred to said fog-producing material to produce a fog which is released to an environment of use through the opening in said canister cap.

* * * * *